United States Patent [19]

Powell et al.

[11] Patent Number: 5,968,368
[45] Date of Patent: Oct. 19, 1999

[54] PURIFICATION PROCESS

[75] Inventors: Richard Llewellyn Powell, Tarporley; Alan John Handley, Widnes; Richard Dominic Clarke, Northwich, all of United Kingdom

[73] Assignee: Imperial Chemical Industries PLC, United Kingdom

[21] Appl. No.: 09/170,869

[22] Filed: Oct. 14, 1998

Related U.S. Application Data

[62] Division of application No. 08/727,462, filed as application No. PCT/GB95/00847, Apr. 13, 1995, Pat. No. 5,824,225.

[30] Foreign Application Priority Data

Apr. 21, 1994 [GB] United Kingdom .................. 9407886

[51] Int. Cl.$^6$ .................................................. B01D 15/08
[52] U.S. Cl. .......................................... 210/656; 210/635
[58] Field of Search ...................... 210/635, 656, 210/659, 198.2, 502.1

[56] References Cited

U.S. PATENT DOCUMENTS

| | | | |
|---|---|---|---|
| 3,914,174 | 10/1975 | Fuchs | 210/656 |
| 3,954,678 | 5/1976 | Marquisee | 252/451 |
| 4,177,038 | 12/1979 | Biebricher | 210/198.2 |
| 4,353,801 | 10/1982 | Mukoyama | 210/635 |
| 4,522,995 | 6/1985 | Anderson | 526/243 |
| 4,597,943 | 7/1986 | Sugiyama | 210/198.2 |
| 4,673,733 | 6/1987 | Chandra | 210/656 |
| 4,767,670 | 8/1988 | Cox | 428/403 |
| 4,787,983 | 11/1988 | Di Foggio | 210/656 |
| 4,802,986 | 2/1989 | Hayes | 210/635 |
| 4,816,159 | 3/1989 | Khosah | 210/198.2 |
| 4,820,044 | 4/1989 | Crighton | 210/198.2 |
| 4,826,603 | 5/1989 | Hayes | 210/635 |
| 4,865,741 | 9/1989 | Nolte | 210/635 |
| 5,246,588 | 9/1993 | Tonelli | 210/656 |
| 5,262,057 | 11/1993 | Tonelli | 210/656 |
| 5,369,165 | 11/1994 | Kato | 524/462 |

FOREIGN PATENT DOCUMENTS

| | | | |
|---|---|---|---|
| 254 610 | 1/1988 | European Pat. Off. | 210/198.2 |
| 538 827 | 4/1993 | European Pat. Off. | 210/198.2 |

OTHER PUBLICATIONS

Suatoni, Hydrocarbon Group Types in Gasoline—Range Materials by HPLC, Journal of Chromatographic Science, vol. 13, Aug. 1975, pp. 367–371.

O'Brien, Studies of Methods for Hydrocarbon Type Analysis of Gasolines, The Analyst, vol. 110, No. 6, Jun. 1985, pp. 593–597.

Chemical Abstracts, vol. 92., No. 4, Abstract No. 92:290575 Jan. 28, 1980.

Bruno, "Retention of Halocarbons", Journal of Chromatography vol. 672, Jun. 1994, pp. 149–158.

*Primary Examiner*—Ernest G. Therkorn

[57] ABSTRACT

A process for purifying a crude material containing one or more desired compounds in impure form id described. The process comprises the steps of (1) passing the crude material through a chromatography column packed with a particulate absorbent solid using a solvent comprising at least one fluorine containing compound selected from the (hydro) fluorocarbons and the (hydro)fluorocarbon ethers to transport the said crude material through the packed column, and (2) collecting the one or more desired compounds as they emerge from the column as a solution in the solvent.

2 Claims, No Drawings

PURIFICATION PROCESS

This is a divisional under 35 U.S.C. section 120 of U.S. Ser. No. 08/727,462 filed on Oct. 18, 1996, now U.S. Pat. No. 5,824,225 which is a 371 application of PCT application PCT/GB95/00847 which designated the United States, filed internationally on Apr. 13, 1995.

The present invention relates to a process for purifying a crude material by liquid chromatography.

The use of liquid chromatography to isolate a desired compound in essentially pure form from a crude material which contains that compound as a constituent part is known in the art. In this known process, the crude material to be separated is charged to the top of a chromatography column containing a finely divided absorbent solid, the so-called stationary phase, and is effectively washed through this column at a controlled rate by means of a flow of solvent, the so-called mobile phase. As the solvent flows through the column, it carries the crude material along with it, but the various components of the crude material are carried along at differing rates owing to the differing degrees of absorption thereof on the column packing. Thus, as the crude material passes through the column it is gradually separated into its component parts, and by careful selection of the packing material and solvent medium the desired compound can be collected off the column in essentially pure form as a solution in the solvent medium.

A particularly efficient form of liquid chromatography is so-called high performance liquid chromatography (HPLC) in which very finely divided solids, e.g. solids having mean particle diameters in the range of from 5 to 10 microns ($\mu$m), are used to pack the column and high pressures, e.g. up to 8000 psi, are employed to drive the solvent through the column so as to achieve a realistic solvent flow rate. The first commercial use of HPLC was as an analytical tool in which only very small quantities of complex organic mixtures were separated in the column. However, more recent developments have enabled HPLC to be used for the isolation/purification of development and even production quantities of a desired compound such as a pharmaceutical product.

The present invention is concerned with the provision of new solvents for use in liquid chromatography techniques, particularly high performance liquid chromatography techniques.

According to one aspect of the present invention there is provided a process for purifying a crude material containing one or more desired compounds in impure form, which process comprises the steps of (1) passing the crude material through a chromatography column packed with a particulate absorbent solid using a solvent comprising at least one fluorine containing compound selected from the (hydro)fluorocarbons and the (hydro)fluorocarbon ethers to transport the said crude material through the packed column, and (2) collecting the one or more desired compounds as they emerge from the column as a solution in the solvent.

According to a further aspect of the present invention there is provided a process for isolating one or more desired compounds from a crude material which contains those compounds as a constituent part, which process comprises the steps of (1) passing the crude material through a chromatography column packed with a particulate absorbent solid using a solvent comprising at least one fluorine containing compound selected from the (hydro)fluorocarbons and the (hydro)fluorocarbon ethers to transport the said crude material through the packed column, and (2) collecting the one or more desired compounds as they emerge from the column as a solution in the solvent.

The present invention also provides for the use of a solvent comprising at least one fluorine containing compound selected from the (hydro)fluorocarbons and the (hydro)fluorocarbon ethers in a liquid chromatography process, particularly a high performance liquid chromatography (HPLC) process.

The crude material to be separated is charged to the inlet end of the packed chromatography column and a supply of the solvent or eluant is then fed to the same end of the packed column. The solvent entrains or dissolves the crude material and carries this material along with it through the column, specifically through the absorbent solid material packing the column. Although the solvent may be allowed to pass passively through the column under the action of gravity, it is much preferred to use a HPLC technique in which the solvent is forcibly driven through the packed column using a pump or some other means to create a positive pressure at the inlet end of the column. The flow of solvent through the column is continued at least until the one or more desired compounds have been eluted from the column. Finally, the desired compound(s) can be recovered by removing the solvent, e.g. by evaporation.

Columns designed for reverse phase or standard phase HPLC may be employed in the process of the present invention.

The particulate absorbent solid which is used to pack the column, i.e. the stationary phase, may be any of the materials which are routinely used for this purpose including coated materials of the type which are used in reverse phase HPLC. Particularly suitable materials include silica and alumina (which may be coated) both of which are available in chromatography grades, including HPLC grades. In the case of HPLC, the particulate absorbent solid used to pack the column will typically have a mean particle diameter in the range of from 0.5 to 20.0 $\mu$m, more typically in the range of from 1.0 to 10.0 $\mu$m. The column packing may be wetted with the solvent prior to charging the crude material to the head of the column.

The solvent which is used to run the chromatography process comprises at least one fluorine containing compound selected from the (hydro)fluorocarbons and the (hydro) fluorocarbon ethers. In this specification, a (hydro) fluorocarbon is a compound selected from the group consisting of the hydrofluorocarbons and the perfluorocarbons and a (hydro)fluorocarbon ether is a compound selected from the group consisting of the hydrofluorocarbon ethers and the perfluorocarbon ethers. The solvent may contain a mixture of two or more fluorine containing compounds, including a mixture containing a (hydro)fluorocarbon and a (hydro)fluorocarbon ether.

Suitable (hydro)fluorocarbons and (hydro)fluorocarbon ethers for the solvent pay have boiling points as high as 200° C. Preferably, however, the (hydro)fluorocarbons and (hydro)fluorocarbon ethers from which the one or more fluorine containing compounds making up the solvent are selected will have a boiling point of 25° C. or below, for example in the range of from −85 to 25° C. Particularly preferred (hydro)fluorocarbons and (hydro)fluorocarbon ethers for the solvent will have a boiling point of 0° C. or below, for example in the range of from −85 to 0° C.

The advantage of using low boiling (hydro)fluorocarbons and (hydro)fluorocarbon ethers is that the removal of such solvents from the compounds which they elute from the chromatography column is relatively facile and can be accomplished by flash evaporation at relatively low temperatures, e.g. room temperature and below.

The preferred solvents comprise one or more fluorine containing compounds selected from the hydrofluorocarbons and the hydrofluorocarbon ethers and, of these, solvents comprising one or more hydrofluorocarbons are particularly preferred.

The preferred hydrofluorocarbon ethers are those having from 2 to 4 carbon atoms, with the fluorine containing dialkyl ethers having from 2 to 4 carbon atoms being particularly preferred and the fluorine containing dimethyl ethers being especially preferred. Examples of $C_{2-4}$ hydrofluorocarbon ethers which may be used for the solvent include, inter alia, trifluoromethyl difluoromethyl ether ($CF_3OCF_2H$), trifluoromethyl fluoromethyl ether ($CF_3OCFH_2$), bis(difluoromethyl) ether ($CF_2HOCF_2H$), trifluoromethyl methyl ether ($CF_3OCH_3$), pentafluoroethyl difluoromethyl ether ($CF_3CF_2OCF_2H$), 1,1,1,2-tetrafluoroethyl trifluoromethyl ether ($CF_3CFHOCF_3$), pentafluoroethyl methyl ether ($CF_3CF_2OCH_3$) and 1,1,2,2-tetrafluoroethyl trifluoromethyl ether ($CF_2HCF_2OCF_3$).

The preferred hydrofluorocarbons for use in the solvent are selected from the $C_{1-3}$ hydrofluorocarbons and particularly the $C_{1-3}$ hydrofluoroalkanes. Examples of $C_{1-3}$ hydrofluoroalkanes which may be used include, inter alia, trifluoromethane, fluoromethane, difluoromethane, pentafluoroethane, 1,1,1-trifluoroethane, 1,1,2,2-tetrafluoroethane, 1,1,1,2-tetrafluoroethane, 1,1,1,2,2,3-hexafluoropropane and 1,1,1,3,3,3-hexafluoropropane. Solvents comprising one or more compounds selected from the hydrofluoromethanes and the hydrofluoroethanes are particularly preferred and, of these, solvents comprising one or more of difluoromethane (R-32), 1,1,1,2-tetrafluoroethane (R-134a) and pentafluoroethane (R-125) are especially preferred. The most preferred solvent for use in the process of the present invention is one comprising 1,1,1,2-tetrafluoroethane.

A fluorine free co-solvent may be blended with the one or more fluorine containing compounds specified above in order to modify their solvent properties and provide a solvent having the required solvent strength. Suitable co-solvents may be selected from the hydrocarbons, the carboxylic acid esters, the ethers, the chlorocarbons, the alcohols, the nitrites, the ketones and the amides. Co-solvents having a boiling point of 100° C. or below are preferred, with co-solvents having a boiling point of 25° C. or below, for example in the range of from −85 to 25° C., being particularly preferred. Especially preferred co-solvents are selected from the hydrocarbons, the hydrocarbon ethers and the (hydro)chlorocarbons which have a boiling point of 25° C. or below, for example in the range of from −85 to 25° C.

Where the (hydro)fluorocarbon or (hydro)fluorocarbon ether is blended with a co-solvent, particularly preferred blends are combinations of a (hydro)fluorocarbon or (hydro) fluorocarbon ether with a co-solvent of comparable boiling point with which they can form an azeotropic or azeotrope-like mixture. Examples of such blends include 1,1,1,2-tetrafluoroethane with dimethyl ether, 1,1,1,2-tetrafluoroethane with butane and 1,1,1,2-tetrafluoroethane with methyl chloride.

In line with normal liquid chromatography practice, the composition of the solvent blend can be varied during the course of a run to enhance the resolution of the separation.

The solvent which is used must, of course, be in liquid form. Where the solvent comprises one or more low boiling compounds which are gases at room temperature, the required liquid form may be attained by cooling the solvent to a suitably low temperature at some point before it enters the column, e.g. at the pump head, or by over-pressurising the container in which the solvent is contained, e.g. by means of an inert gas such as helium.

In the case of HPLC, elevated pressures are employed to drive the solvent through the column. Typically, pressures in the range of from 200 to 12,000 psi. more typically in the range of from 600 to 3000 psi are used.

The apparatus which is used to carry out the liquid chromatography process may employ a solvent recovery system which removes the solvent from the eluate after it has emerged from the column by evaporation and then condenses the resulting solvent vapour for return to the inlet end of the column usually via a solvent reservoir.

A suitable recovery system for low boiling point solvents, by which we mean solvents having a boiling point of 25° C. or below, e.g. 0° C. or below, comprises an evaporator into which the eluate emerging from the chromatography column is passed, a compressor for compressing the vapour generated in the evaporator and a condenser for cooling the compressed vapour emerging from the compressor. The solvent is removed from the eluate in the evaporator by flash evaporation induced by suction from the compressor and the solvent vapour so generated then passes to the compressor, which may be a diaphragm compressor, where it is compressed. From the compressor, the solvent vapour passes to the condenser where it is cooled and returned to liquid form for recharging to the column inlet or possibly to a solvent reservoir supplying solvent to the column inlet. The condenser, which may take the form of a coiled tube, can be arranged inside the evaporator so that the latent heat of condensation provides at least some of the energy required to evaporate the solvent, the remainder being supplied by the work done by the compressor.

A further suitable recovery system for low boiling point solvents comprises a solvent recycling circuit comprising an evaporator into which the eluate emerging from the chromatography column is passed and in which the solvent is evaporated and a condenser in which the vapour emerging from the evaporator is cooled and returned to liquid form for recharging to the column inlet or possibly to a solvent reservoir supplying solvent to the column inlet. Heating of the evaporator and cooling of the condenser may be carried out independently, but in a preferred embodiment an external heat pump system is used to both heat the evaporator and to cool the condenser. The external heat pump system comprises an evaporator, a compressor, a condenser and an expansion valve which are sequentially arranged in a circuit through which a heat transfer fluid is caused to flow. The evaporator of the external heat pump system, which may take the form of a coiled tube, is arranged inside or around the outside of the condenser of the solvent recycling circuit so that evaporation of the heat transfer fluid in the evaporator cools the condenser and provides for the condensation of the solvent vapour passing through the solvent recycling circuit. The vapour generated in the evaporator of the external heat pump system is then compressed and passes to the condenser where it condenses and gives off heat. The condenser of the external heat pump system, which may also take the form of a coiled tube, is arranged inside or around the outside of the evaporator of the solvent recycling circuit so that the latent heat of condensation associated with the condensation of the heat transfer fluid provides the heat required to evaporate the solvent passing through the solvent recycling circuit. The condensed heat transfer fluid is then returned through an expansion valve to the evaporator so completing the cycle in the external heat pump system.

The liquid chromatography process of the present invention may be used in any of the usual applications for liquid chromatography including enantiomer separation using a chiral column.

The present invention is now illustrated but not limited by the following example.

Example 1

High performance liquid chromatography was used to separate an organic mixture comprising naphthalene, anthracene and biphenyl using 1,1,1,2-tetrafluoroethane (R-134a) as the solvent and Spherisorb S50DS2 as the column packing. The organic mixture (dissolved in dichloromethane) was charged to the inlet of the packed chromatography column and the flow of R-134a was then commenced with the pump being adjusted to give a solvent flow rate of 2 ml/minute. The R-134a was liquefied by over-pressurising the cylinder in which it was contained with helium. The material emerging from the column was passed through a UV detector to detect the presence of the naphthalene, anthracene and biphenyl. The organic mixture was separated into its component parts and the naphthalene, anthracene and biphenyl were detected as discrete species.

We claim:

1. A process for performing a liquid chromatography process comprising passing a solvent comprising at least one hydrocarbon selected from the group consisting of trifluoromethane, fluoromethane, difluoromethane, pentafluoroethane, 1,1,1-trifluoroethane, 1,1,2,2-tetrafluoroethane, 1,1,1,2-tetrafluoroethane, 1,1,1,2,2,3-hexa-fluoropropane and 1,1,1,3,3,3-hexafluoropropane through a chromatography column.

2. A process for performing a high performance liquid chromatography process comprising passing a solvent comprising at least one hydrocarbon selected from the group consisting of trifluoromethane, fluoromethane, difluoromethane, pentafluoroethane, 1,1,1-trifluoroethane, 1,1,2,2-tetrafluoroethane, 1,1,1,2-tetrafluoroethane, 1,1,1,2,2,3-hexa-fluoropropane, 1,1,1,3,3,3-hexafluoropropane through a high performance chromatography column.

* * * * *